United States Patent [19]
von Alfthan et al.

[11] Patent Number: 4,876,902

[45] Date of Patent: Oct. 31, 1989

[54] METHOD FOR DRAWING SAMPLES FROM MATERIAL CONTAINING SOLID INGREDIENTS

[75] Inventors: George C. von Alfthan, Espoo; Jorma T. Helanniemi, Helsinki, both of Finland

[73] Assignee: Outokumpu Oy, Helsinki, Finland

[21] Appl. No.: 184,408

[22] Filed: Apr. 21, 1988

[30] Foreign Application Priority Data

Apr. 23, 1987 [FI] Finland ................................ 871781

[51] Int. Cl.$^4$ .............................................. G01N 1/14
[52] U.S. Cl. .................................................. 73/863.83
[58] Field of Search ....................... 73/863.41–863.45, 73/863.51–863.58, 863.71, 863.72, 863.81–863.86, 864.34, 864.35, 864.73, 863.83

[56] References Cited

U.S. PATENT DOCUMENTS

| | | | |
|---|---|---|---|
| 4,008,620 | 2/1977 | Narato et al. | 73/864.34 |
| 4,091,835 | 5/1978 | Frampton | 73/863.51 |
| 4,134,289 | 1/1979 | Bohl et al. | 73/864.34 |
| 4,426,888 | 1/1984 | Smith | 73/863.83 |

FOREIGN PATENT DOCUMENTS

| | | | |
|---|---|---|---|
| 0106765 | 4/1984 | European Pat. Off. | |
| 0237342 | 11/1985 | Japan | 73/863.81 |
| 0471307 | 5/1975 | U.S.S.R. | 73/863.51 |
| 0583383 | 12/1977 | U.S.S.R. | 73/863.83 |
| 0828004 | 5/1981 | U.S.S.R. | 73/863.51 |
| 2010778 | 7/1979 | United Kingdom. | |

*Primary Examiner*—Robert R. Raevis
*Attorney, Agent, or Firm*—Dellett, Smith-Hill and Bedell

[57] ABSTRACT

The invention relates to an apparatus for drawing samples from material containing solid particles, which material is in a flowing motion. In the apparatus, the sampling member (3, 13, 24) is connected to an adjusting device (4, 15, 26) and a suction member (6, 17, 25) so that the material flow coming from the sampling member (3, 13, 24) by means of the adjusting device (4, 15, 26) can be directed via the suction member (6, 17, 25) to form the sample.

9 Claims, 2 Drawing Sheets

METHOD FOR DRAWING SAMPLES FROM MATERIAL CONTAINING SOLID INGREDIENTS

BACKGROUND OF THE INVENTION

The present invention relates to a method for drawing samples from material containing essential amounts of solid particles, which material is advantageously in a flowing motion, or can be set to a flowing motion.

According to the generally known practice, a sample is drawn from material flowing in a pipe with a large diameter so that on the bottom surface or on the side of the said pipe there is made an aperture, and part of the flow is conducted out of the pipe via this aperture, through a tube with a small diameter and by means of a sampling member. If the flowing material has a high solids content, the use of a tube of the described type, which generally forms an angle of 90°, causes a danger of blocking if the sample flow is stopped.

The object of the present invention is to remove some of the drawbacks of the prior art and to achieve a sampling apparatus which is securer in operation, for drawing samples from materials containing essential amounts of solid particles, so that the danger of blocking caused by these solid particles can be advantageously reduced.

SUMMARY OF THE INVENTION

According to the invention, the sampling apparatus comprises a sampling member as well as members for sucking the sample and for conducting it further to be processed in an analyzer. The sampling member is advantageously placed in a flow which proceeds for example in the horizontal direction, so that the solids content is highest in the bottom section of the flow, and the danger of blocking consequently highest when prior art equipment is employed.

The sampling apparatus is advantageously composed of a sampling member and of a flow adjusting device connected thereto, whereby the sample amount flowing through the sampling member into the suction member can be adjusted. The sampling apparatus of the invention can be placed either partly or totally below the surface of the flow.

When a sample should be drawn from a material flow advantageously containing solid particles and by means of the apparatus of the present invention, a low pressure is created in the sample suction member connected to the sampling member for instance by means of an ejector-type or other pressure control member, such as an air lift. When advantageous pressure conditions have been established in the suction member, the flow adjusting device, located in the connecting duct between the suction member and the sampling member, is opened, and simultaneously the flow proceeding through the sampling member is adjusted by closing the control member connected to the sampling member. Because the connecting duct between the sampling member and the suction member is advantageously installed in between the sampling member and the adjusting device, the flow which has entered into the sampling member proceeds advantageously to the suction member via the connecting duct when an advantageous, desired amount of the sample has entered the suction member, the flow adjusting device, i.e. the faucet, provided in the connecting duct is closed, and the adjusting device sucked against the sampling member is opened. Thus the material flow proceeds again relatively freely through the sampling member and removes any solid particles that have possibly stuck to the pipe walls in connection with the sampling, thus preventing the blocking of the sampling member. The sample obtained in the suction member is in turn conducted, via another connecting duct attached to the suction member, further to an analyzer. In order to speed up the flowing of the sample, to the connecting duct there is advantageously conducted some pressurized gas or other similar medium, by means of which the duct is simultaneously cleared of the sample.

According to the invention, the flow adjusting devices of the sampling apparatus may be operated for instance pneumatically, hydraulically or electrically. Furthermore, the number of apparatuses placed in one material flow may be one or several, and they may also be placed essentially on the same spot and parallel with respect to the material flow.

BRIEF DESCRIPTION OF THE DRAWINGS

The invention is explained in more detail below, with reference to the appended drawing where.

DETAILED DESCRIPTION

Figure 1:
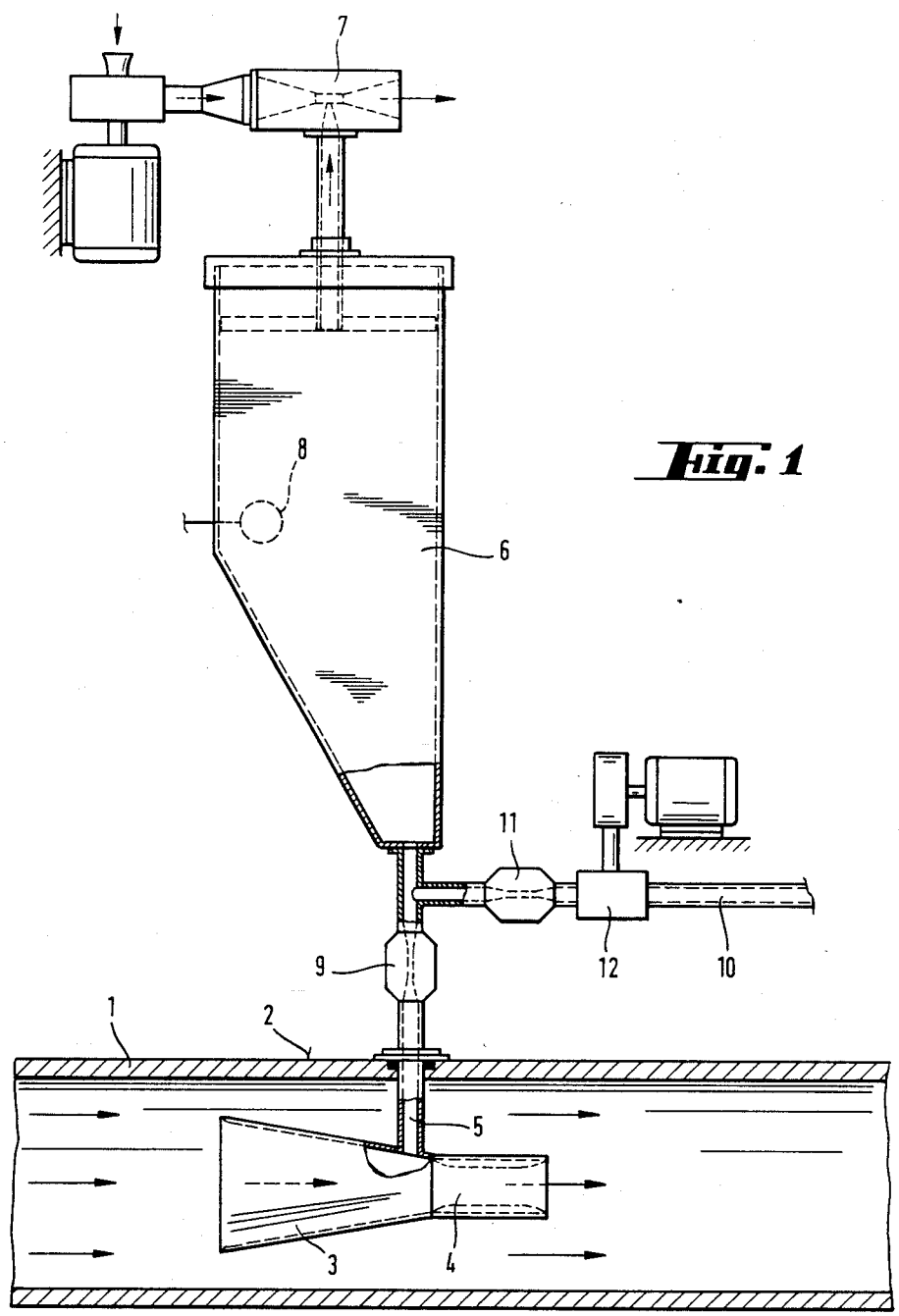
FIG. 1 is a side-view illustration of a preferred embodiment of the invention, seen in partial cross-section.

According to FIG. 1, the slurry containing solid ingredients flows in the pipe 1. In order to draw a sample from this flow, inside the pipe 1 there is installed, through the sealed aperture located on the top surface 2 of the pipe 1, the sampling member 3 of the invention, which is essentially slot-like in cross-section, as well as the flow adjusting member 4, advantageously for instance a rubber tube valve, which is attached immediately after the sampling member. Via the pipe 5, the sampling member 3 is connected to the intermediate tank 6 of the sample, which tank is located outside the flow. The tank 6 is further provided with an ejector 7 in order to reduce pressure in the tank to the desired level, and a sample surface height regulator 8.

When drawing a sample from the material flowing in the pipe 1, a low pressure is created in the tank 6 by means of the ejector 7. Thereafter the faucet 9 located in the intermediate pipe 5 is opened, at the same time as the rubber tube valve 4 within the pipe 1 is closed. Thus the material flow entering the sampling, member 3 is directed, through the pipe 5, to the intermediate tank 6. When the amount of the obtained sample is sufficient, i.e. the sample surface has reached the desired level by means of the surface height regulator 8, the faucet 9 is closed and the rubber tube valve is opened. Thus the material flow entering the sampling member 3 is directed, via the open rubber tube valve 4, back to the mainstream of the material, at the same time keeping the sampling member 3 clear of possible solid particle accretions.

The sample conducted into the intermediate tank 6 is further directed, via the pipe 10 connected to the intermediate tank, to the analyzer, after the faucet 11 provided in the pipe 10 has been opened. Some pressurized medium can be further conducted to the pipe 10 through the valve 12 in order to speed up the sample transport.

Figure 2:
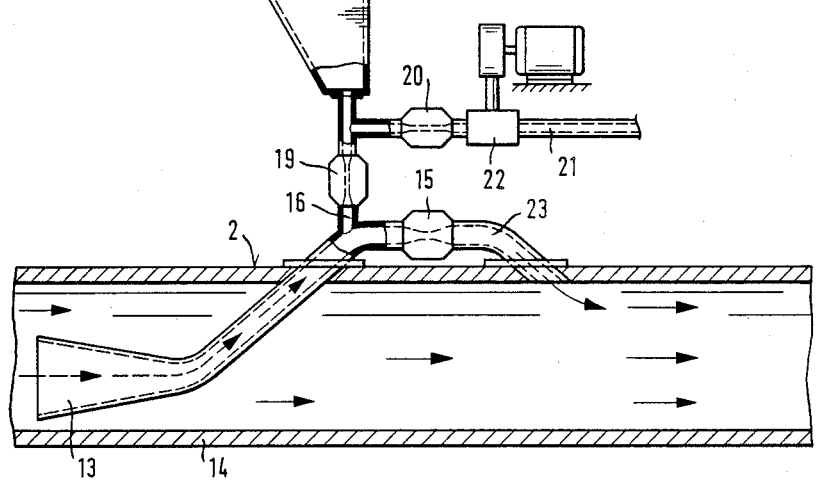
FIG. 2 is a side-view illustration of another preferred embodiment of the invention, seen in partial cross-section.

In the preferred embodiment of FIG. 2, the sampling member 13 is placed at least partly underneath the flowing surface of the material flowing in the pipe 14. The flow adjusting member 15 of the sampling member in turn is placed outside the pipe 14. The sampling member 13 is designed so that it directs the sample flow through the sealed aperture provided In the pipe 14 to outside the pipe 14 and further onto the adjusting device 15. The sampling member 13 is still connected to the intermediate tank 17, essentially similar to the one illustrated in FIG. 1, by means of the pipe 16.

When drawing a sample from the material flowing in the pipe 14 by employing the apparatus of FIG. 2, the ejector 18 is used for creating a low pressure in the intermediate tank 17 in an essentially similar fashion as in the embodiment of FIG. 1. Likewise the other operations of the apparatus of FIG. 2 correspond in all essential features to those of the embodiment of FIG. 1. In order to make operation possible, the pipe 1 6 is provided with a faucet 19, and a faucet 20 is installed in the pipe 21 connecting the intermediate tank 17 to the analyzer. The pipe 21 is also provided with a member 22 in order to feed the medium possibly needed for speeding up the flow.

If a sample is not drawn from the material flowing in the pipe 14, the flow entering the sampling member 13 is conducted, via the adjusting device 15, advantageously back into the pipe 14 through the connecting duct 23 provided therein.

Figure 3:
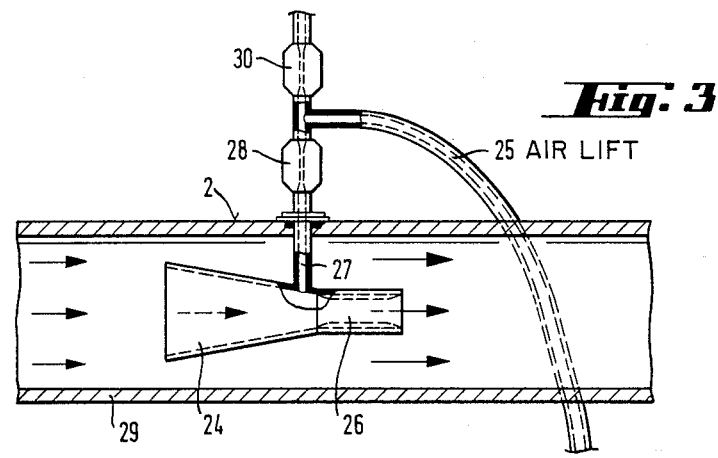
FIG. 3 is a side-view illustration of a third preferred embodiment of the invention, seen in partial cross-section.

According to FIG. 3, the sampling member 24 is provided with a suction member 25 operated according to the air-lift principle. The sample flow from the sampling member 24 is controlled by means of the adjusting device 26. If the sample is desired to be conducted into the suction member 25 and further to the analyzer, the adjusting member 26 is closed simultaneously as the faucet 28 provided in connection with the connecting duct 27 between the sampling member and the suction member is opened. After the desired sample amount has flowed through the suction member 25 to be analyzed, the faucet 28 is closed, whereas the adjusting member 26 is simultaneously opened, so that the material flow from the sampling member 24 is directed back to the rest of the material flow, into the pipe 29. In order to realize the operation of the suction member 25 in an advantageous fashion, in connection with the suction member 25 there is provided a connecting member 30, through which the pressure conditions enabling the flow are adjustable by means of some medium such as water.

We claim:

1. An apparatus for drawing a sample from a flow of slurry material, comprising:
   a sampling member defining a passage having a first end and a second end, the sampling member being adapted to be place with the first and second ends of the passage both in direct open communication with the flow of slurry and the first end upstream of the second end,
   a flow control device having a first state in which it permits flow of slurry through the passage and a second state in which it prevents such flow, and
   suction means coupled to the passage defined by the sampling member at a location between the flow control device and the first end of the passage, for extracting slurry material from the passage when the flow control device is in its second state.

2. The apparatus of claim 1, wherein the flow control device is a rubber tube valve.

3. The apparatus of claim 1, wherein the suction means comprise an ejector.

4. The apparatus of claim 1, wherein the suction means comprise an air lift.

5. The apparatus of claim 1, comprising a sampling conduit connecting the sampling member to the suction means.

6. The apparatus of claim 5, comprising an intermediate tank connected to the sampling conduit, and wherein the suction means are in communication with the intermediate tank for establishing a selected pressure therein.

7. The apparatus of claim 6, comprising a valve connected in the sampling conduit between the sampling member and the intermediate tank, and a second conduit connected to the sampling conduit between the valve and the intermediate tank and provided with a valve for selectively removing slurry material from the intermediate tank by way of the second conduit.

8. The apparatus of claim 5, wherein the sampling member is generally frusto-conical and the suction means comprise a vessel that defines an interior space and means for placing the interior space of the vessel at a selected pressure.

9. An apparatus for conducting a slurry material from a first location to a second location, comprising:
   a duct through which the slurry material flows from the first location to the second location,
   a sampling member defining a passage having a first end and a second end, the first and second ends of the passage being in direct open communication with the interior space of the duct at locations spaced apart along the duct, whereby slurry material flowing from the first location to the second location may enter the passage at the first end thereof and leave the passage at the second end thereof,
   a flow control device located inside the duct and having a first condition in which it permits flow of slurry material through the passage and a second condition in which it prevents flow of slurry material through the passage,
   a sampling conduit connected to the sampling member at a location between the flow control device and the first end of the sampling member, and
   suction means connected to the sampling conduit for drawing slurry material from the passage.

* * * * *